(12) United States Patent
Cho et al.

(10) Patent No.: US 12,263,062 B2
(45) Date of Patent: Apr. 1, 2025

(54) THREE-DIMENSIONAL INTRAORAL SCANNER

(71) Applicant: MEDIT CORP., Seoul (KR)

(72) Inventors: Eun Gil Cho, Gunpo-si (KR); Seung Jin Lee, Gunpo-si (KR)

(73) Assignee: MEDIT CORP., Seoul (KR)

( * ) Notice: Subject to any disclaimer, the term of this patent is extended or adjusted under 35 U.S.C. 154(b) by 622 days.

(21) Appl. No.: 17/530,528

(22) Filed: Nov. 19, 2021

(65) Prior Publication Data

US 2022/0079717 A1    Mar. 17, 2022

Related U.S. Application Data

(63) Continuation of application No. PCT/KR2020/006652, filed on May 21, 2020.

(30) Foreign Application Priority Data

May 21, 2019    (KR) ........................ 10-2019-0059581

(51) Int. Cl.
   *A61C 9/00*     (2006.01)
   *A61B 1/00*     (2006.01)
   *A61B 1/24*     (2006.01)
(52) U.S. Cl.
   CPC ........ *A61C 9/0053* (2013.01); *A61B 1/00186* (2013.01); *A61B 1/24* (2013.01)
(58) Field of Classification Search
   None
   See application file for complete search history.

(56) References Cited

U.S. PATENT DOCUMENTS

2018/0098691 A1    4/2018    Wang et al.

FOREIGN PATENT DOCUMENTS

| CN | 101822526 A | 9/2010 |
| CN | 104799812 A | 7/2015 |

(Continued)

OTHER PUBLICATIONS

Non-final Office Action mailed Dec. 27, 2023 from the Chinese Patent Office for Chinese Application No. 202080036942.9.

(Continued)

*Primary Examiner* — Bao-Luan Q Le
*Assistant Examiner* — Danell L Owens
(74) *Attorney, Agent, or Firm* — Insight Law Group, PLLC; Seung Lee

(57) ABSTRACT

The present invention relates to a three-dimensional intraoral scanner specifically comprising: a case which can be inserted into and withdrawn from the oral cavity, and has an opening portion which is open to allow the form of the inside of the oral cavity (hereinafter, referred to as an 'image') to be incident into the case in the form of light via an end portion thereof; at least one camera which is arranged inside the case to transmit the light incident via the opening portion of the case; a light projector which is arranged on one side of the at least one camera and emits light into the oral cavity via the opening portion; and a single polarized filter which positioned between the at least one camera and the opening portion at a position spaced a set distance (d) from the front end of the at least one camera. Thus, the present invention provides the advantages of making it possible to manufacture a product having a slim size and improve the reliability with which an object to be measured can be measured.

11 Claims, 12 Drawing Sheets

(56) References Cited

FOREIGN PATENT DOCUMENTS

| CN | 106491082 A | 3/2017 | |
|---|---|---|---|
| JP | 2009165831 A | 7/2009 | |
| JP | 2012-512678 A | 6/2012 | |
| KR | 101524605 B1 | 6/2015 | |
| KR | 20160133112 A | 11/2016 | |
| KR | 10-2017-0077432 A | 7/2017 | |
| KR | 20170077432 A | 7/2017 | |
| KR | 101874547 B1 | 7/2018 | |
| WO | WO-2015130071 A1 * | 9/2015 | ........... A61B 5/0062 |

OTHER PUBLICATIONS

Extended Search Report mailed Jan. 5, 2023 for European Application No. 201810303.6.

International Search Report mailed Sep. 1, 2020 for International Application No. PCT/KR2020/006652 and its English translation.

* cited by examiner

THREE-DIMENSIONAL INTRAORAL SCANNER

TECHNICAL FIELD

The present disclosure relates to a three-dimensional (3D) intraoral scanner and, more particularly, to a 3D intraoral scanner able to easily measure an object to be measured using at least one camera.

BACKGROUND ART

In general, an intraoral scanner is an optical device configured to be inserted into the oral cavity of a dental patient to scan the teeth in a non-contact manner so as to generate a 3D scanning model of a row of teeth.

A conventional technology for obtaining 3D information using an image obtained from multiple viewpoints using a single camera includes matching pieces of image information continuously obtained by a method of obtaining distance information between an object and the camera using coordinate systems of images in different viewpoints to find identical objects in the images and then extracting distance information of the objects using projection. Thus, it is difficult to process 3D information, and the problem of the increased quantity of computation is caused. Recently, a stereo vision method using images obtained by two or more cameras is applied to intraoral scanners.

However, in the case of 3D data measurement using the stereo vision method, at least two cameras are required. Since the two cameras must face a measurement object, i.e., an object to be measured, in the same orientation, the use of the inner space of the intraoral scanner for accommodating the two cameras is limited, which is problematic. The size of a product is also increased, thereby causing designing and fabrication of an instrument to be difficult.

FIG. 1 is schematic views illustrating acquisition of 3D information using an intraoral scanner and an application of polarizer plates.

In general, in order to form a 3D scanning model of teeth in the oral cavity using an intraoral scanner, as illustrated in FIG. 1 (a), a method of projecting structured light onto a measurement object O, i.e., a tooth, and obtaining light reflected therefrom, thereby obtaining 3D data, is used.

That is, light generated by a light generator 170 passes through a projection lens 171, is reflected from inside the oral cavity including the measurement object O, i.e., the tooth, and enters through a camera lens 121, so that 3D data is obtained by an imaging sensor 130.

In order to obtain precise surface data of the tooth in this manner, it is important that projected structured light is accurately projected onto the tooth, i.e., the surface of the measurement object O, and the projected light is obtained. However, differently from a surface reflection material, such as a gypsum model, on the surface of which projected light is reflected, in case of an internal reflection material, such as the tooth, light projected onto a measurement object is not only reflected from the surface of the measurement object but also penetrates into the material and is reflected from inside the material. The effect of such internal reflection causes a technical problem in that accurate 3D data cannot be obtained.

In order to overcome this problem, methods (e.g., a method of using a polarizer plate) of obtaining light only reflected from the surface of an internal reflection material of a measurement object using optical wave properties have been studied and developed. However, even in the case that the polarizer plate is used, applications are difficult due to precise axis adjustment for preventing 3D data loss and surface reflection of the polarizer plate.

Furthermore, even in the case that the polarizer plate is applied, as illustrated in FIG. 1 (b), a first polarizer plate 180a must be provided on a projection path before light is projected onto the measurement object O by the light generator 170 and a second polarizer plate 180b must be provided on an incident path before the light reflected from the measurement object O enters the camera lens 121. This means that at least two polarizer plates 180a and 180b must be provided for a single camera, and when the stereo vision method is applied, at least three polarizer plates must be provided. Therefore, it is extremely difficult to design products to be slim, which is problematic.

DISCLOSURE

Technical Problem

Various embodiments are directed to a 3D intraoral scanner configured to obtain 3D image data of a measurement object simultaneously with measuring the measurement object, wherein a body housing may be fabricated to be slim so that a user may easily hold the body housing.

In addition, also provided is a 3D intraoral scanner configured to remove internal reflection light produced by an internal reflection material, such as tooth, when measuring a measurement object, thereby obtaining a clearer and more precise measurement.

Furthermore, also provided is a 3D intraoral scanner able to provide an optimum design plan by which a tip housing configured to be inserted into and withdrawn from the oral cavity of a patient may be fabricated to be slim and a ghost image or noise may be prevented.

The technical problems of the present disclosure are not limited to the above-described problems, and other technical problems which are not described will be clearly understood by those skilled in the art, based on the following descriptions.

Technical Solution

According to an embodiment of the present disclosure, provided is a three-dimensional (3D) intraoral scanner including: a housing configured to be inserted into and withdrawn from an oral cavity, and including an open area in one end thereof, the open area allowing an internal shape (hereinafter, referred to as an image) of the oral cavity to enter the housing as light; at least one camera disposed inside the housing, and configured to allow light entering through the open area of the housing to pass therethrough; a light projector disposed on one side of the at least one camera to emit light into the oral cavity through the open area; and a single polarizer filter located between the at least one camera and the open area, and including a single polarizer filter located in a position spaced apart a set distance (d) from a front end of the at least one camera.

Here, the set distance (d) may be set to a distance in which a projection angle of view, at which light is projected into the oral cavity by the light projector, and an image angle of view, at which light reflected from inside the oral cavity enters the at least one camera, may not overlap with each other.

In addition, the set distance (d) may be set such that light projected into the oral cavity by the light projector does not enter the at least one camera as reflection light reflected by the single polarizer filter.

In addition, the set distance (d) may set to a position in which the entire size of the single polarizer filter is smallest on the premise that the vertical width and the lateral width (hereinafter, briefly referred to as the "entire size") of the single polarizer filter increase as the single polarizer filter is closer to the at least one camera.

In addition, the set distance (d) may meet the following formula:

$$d < \frac{\left(l_i Q_t - \frac{D}{2}\right)}{2\tan\alpha} + \frac{(l_p - l_i)}{2},$$

where d is the set distance, $l_p$ is a distance from the light projector to the image, $l_i$ is a distance from the lens of the camera on one side to the image, $Q_t$ is a triangulation angle, D is the diameter of the lens of the camera on one side, and α is a projection angle of view.

In addition, the housing may include: a body housing in which the at least one camera and a variety of electronic components for driving the at least one camera are disposed; and a tip housing coupled to one end of the body housing, the open area being provided in the tip housing, wherein the single polarizer filter is disposed such that the set distance (d) is positioned in the tip housing.

In addition, a top fitting rib and a bottom fitting rib may be integrally provided inside the tip housing, with top and bottom ends of the single polarizer filter being fitted to the top fitting rib and the bottom fitting rib.

In addition, the tip housing in which the set distance (d) is positioned may be fabricated in a variety of specifications to be provided with a dark room having different lengths depending on a length measured from one end to the other end, and may be detachably coupled to one end of the body housing so as to facilitate detachment from and replacement to one end of the body housing.

In addition, the tip housing may be configured such that the single polarizer filter is previously fixed in different positions meeting the set distance (d) depending on the length of the dark room.

According to another embodiment of the present disclosure, a 3D intraoral scanner may include: a housing configured to be inserted into and withdrawn from an oral cavity, and including an open area in one end thereof, the open area allowing an internal shape (hereinafter, referred to as an image) of the oral cavity to enter the housing as light; at least one camera disposed inside the housing, and configured to allow light entering through the open area of the housing to pass therethrough; a light projector disposed on one side of the at least one camera to emit light into the oral cavity through the open area; and a single polarizer filter located between the at least one camera and the open area, and horizontally disposed such that a projection angle of view projected into the oral cavity by the light projector and an image angle of view reflected from inside the oral cavity and entering the at least one camera do not overlap with each other.

According to another embodiment of the present disclosure, a 3D intraoral scanner may include: a housing configured to be inserted into and withdrawn from an oral cavity, and including a reflecting member reflecting incoming light entering the body housing and exiting light emitted from inside the body housing; a pair of stereo cameras disposed inside the housing, and configured to allow the incoming light entering through the reflecting member of the housing to pass therethrough along different paths; a light projector disposed between the pair of stereo cameras, and configured to emit the exiting light into the oral cavity through the reflecting member; and a single polarizer filter located between the pair of stereo cameras and the reflecting member, and disposed parallel to the light projector.

Advantageous Effects

The 3D intraoral scanner according to an embodiment of the present disclosure may obtain a variety of effects as follows.

First, the imaging board on which the imaging sensor is attached is coupled to the inner side wall of the body housing to refract or change incoming light. Thus, the body housing can be fabricated to be slim such that a user can easily hold the body housing.

Second, image data produced from a measurement object can be accurately scanned using the single polarizer filter without loss, thereby improving the reliability of a product.

Third, an optimum position design plan for the single polarizer filter can be proposed, and thus, the tip housing to be inserted into the oral cavity of a patient can be designed to be slim.

DESCRIPTION OF REFERENCE NUMERALS OF DRAWINGS

Figure 1:
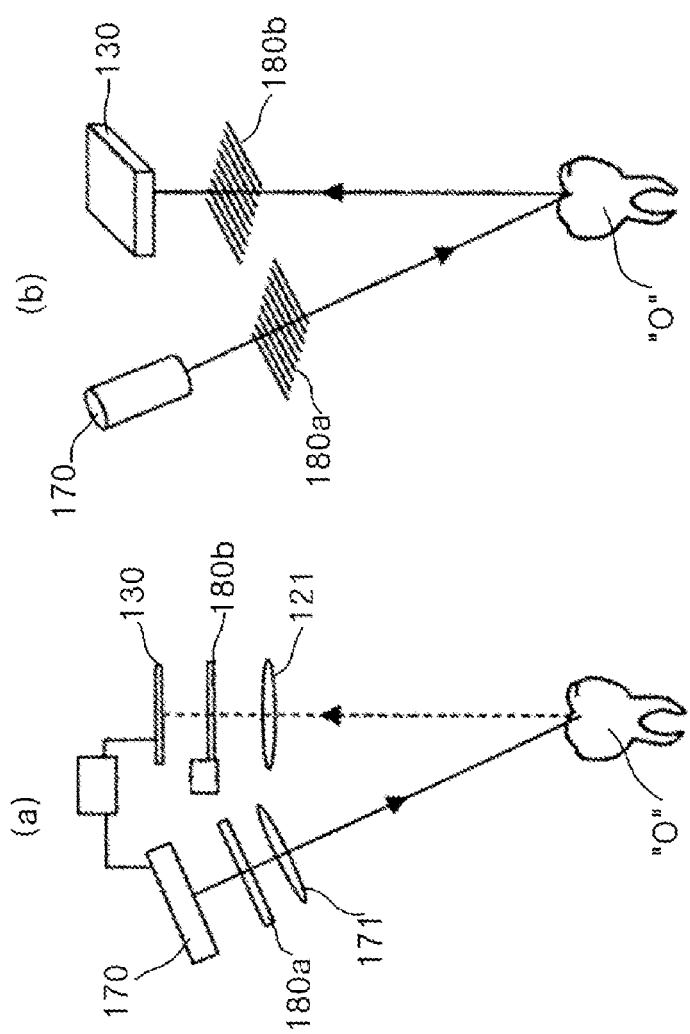
FIG. 1 is schematic views illustrating acquisition of 3D information using an intraoral scanner and an application of polarizer plates.

1: 3D intraoral scanner
10: housing

11: body housing
12: lower housing
13: upper housing
14: tip housing
16: open area
17: exiting light path portion
20: pair of stereo cameras
21: one stereo camera
22: the other one stereo camera
31a, 32a: imaging board
31b, 32b: imaging sensor
41, 42 light path changing mirror
50: camera mount
51, 52: incoming light path portion
53: exiting light path portion
60: reflecting member
70: light projector
80: single polarizer filter
81: bottom fitting rib
91: projection angle of view
92a, 92b: image angle of view
100: measurement object

MODE FOR INVENTION

Hereinafter, some embodiments of the present disclosure will be described in detail with reference to the accompanying drawings. In the following descriptions, like reference numerals designate like elements although the elements are shown in different drawings. Further, detailed descriptions of known functions and configurations incorporated herein will be omitted for the purpose of clarity and for brevity.

In addition, terms, such as first, second, A, B, (a), or (b), may be used herein when describing elements of embodiments of the present disclosure. Each of these terminologies is not used to define an essence, order, or sequence of a corresponding element but used merely to distinguish the corresponding element from other elements. Unless otherwise specified, all terms including technical and scientific terms used herein have the same meaning as that commonly understood by those skilled in the technical field to which the present disclosure pertains. It will be further understood that terms, such as those defined in commonly used dictionaries, should be interpreted as having a meaning that is consistent with their meaning in the context of the relevant art, and will not be interpreted in an idealized or overly formal sense unless expressly so defined herein.

Figure 2:
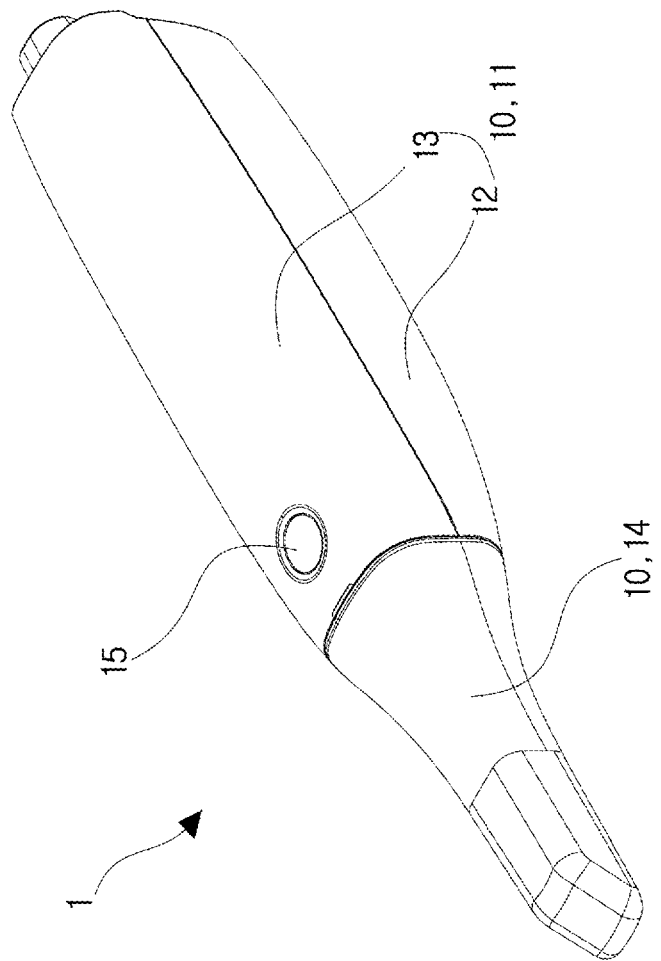
FIG. 2 is a perspective view illustrating a 3D intraoral scanner according to an embodiment of the present disclosure.
Figure 3:
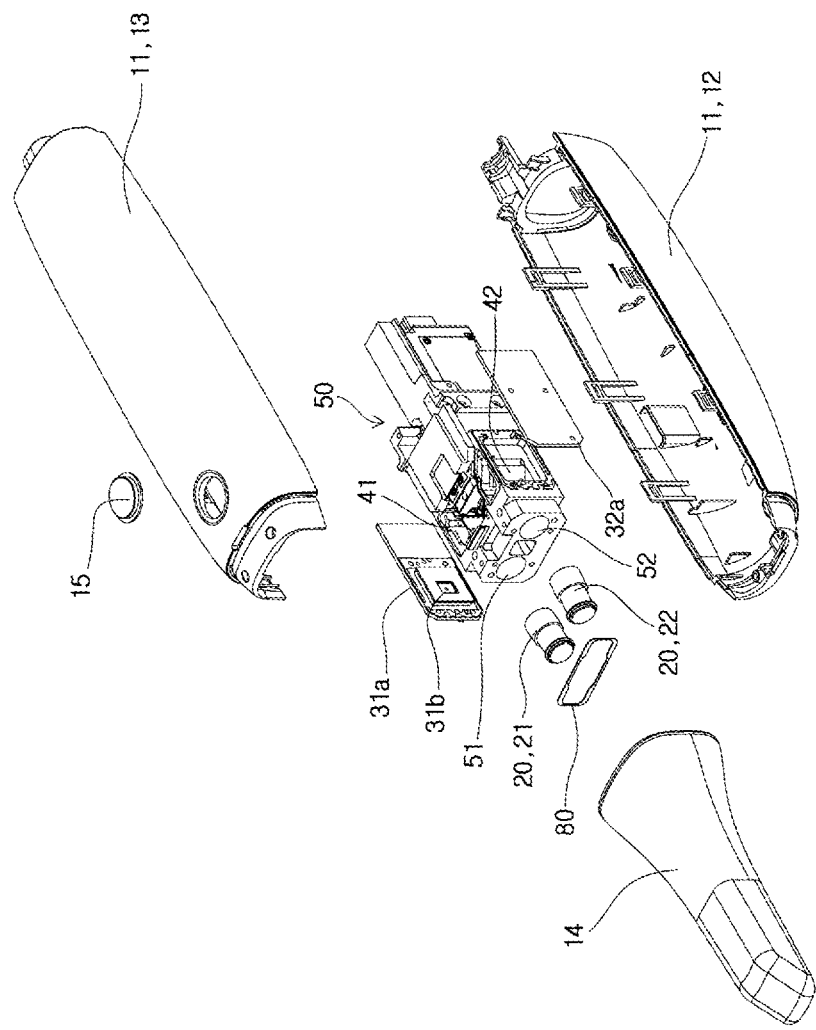
FIG. 3 is an exploded perspective view of FIG. 2.
Figure 4:
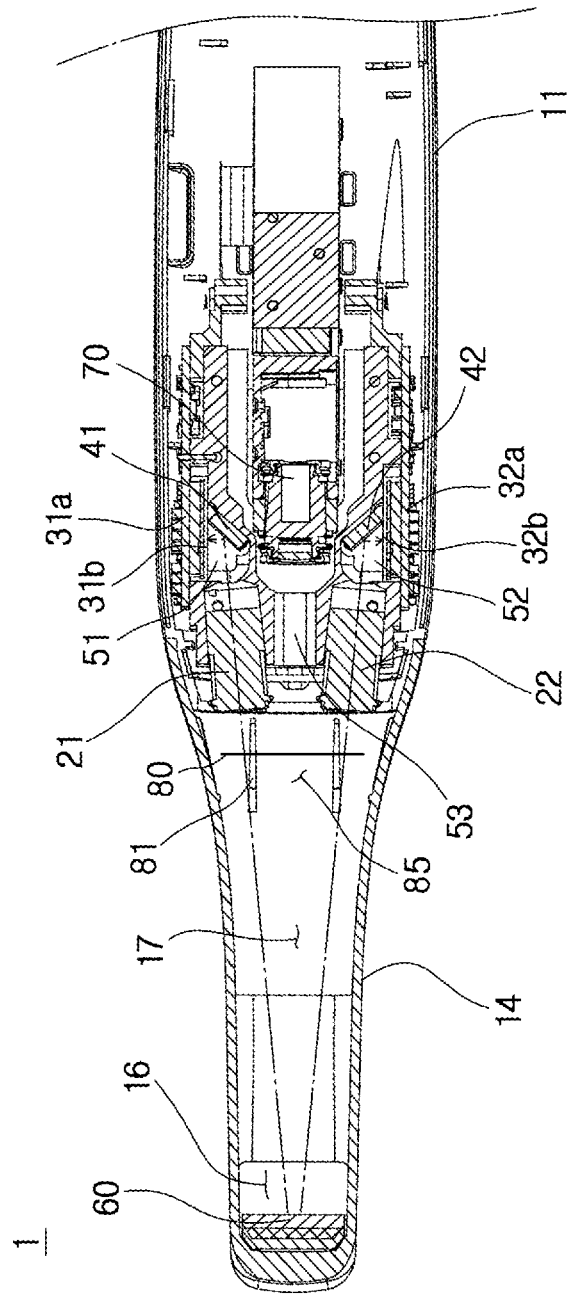
FIG. 4 is a cross-sectional view taken along the line A-A in FIG. 2.
Figure 5:
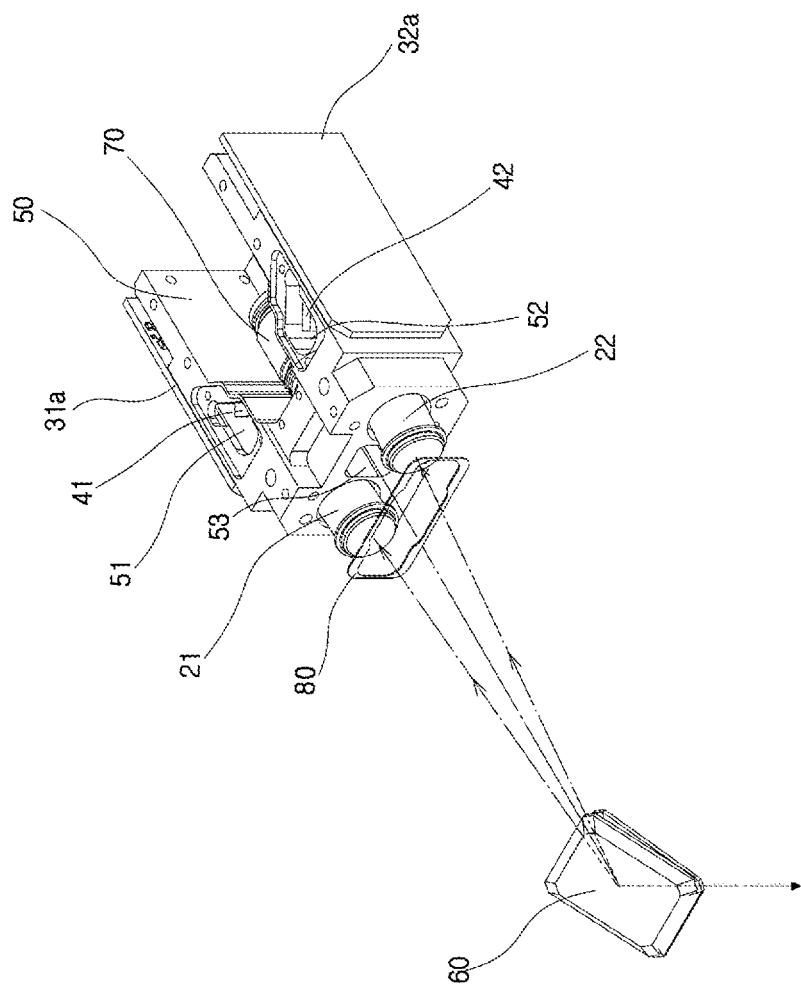
FIG. 5 is a perspective view illustrating an optical path using a pair of stereo cameras among the components illustrated in FIG. 2.
Figure 6:
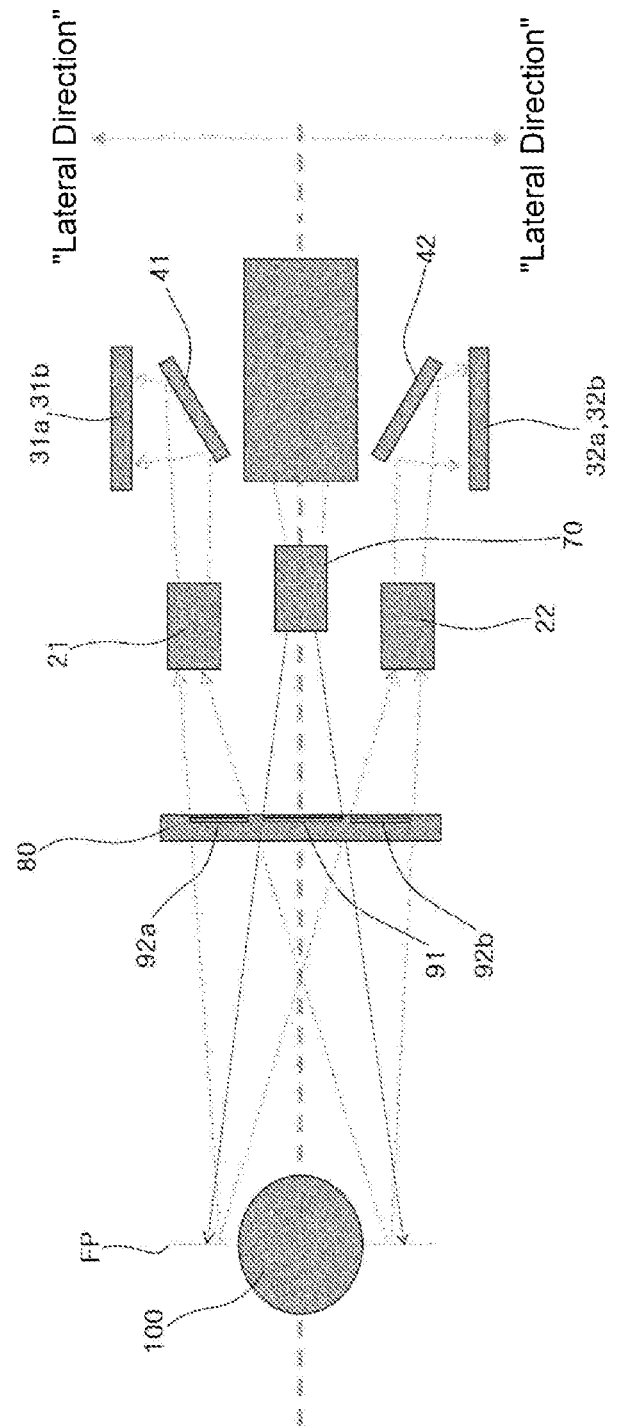
FIG. 6 is a plan schematic view illustrating the position design of a single polarizer filter among the components illustrated in FIG. 2.

FIG. 2 is a perspective view illustrating a 3D intraoral scanner according to an embodiment of the present disclosure, FIG. 3 is an exploded perspective view of FIG. 2, FIG. 4 is a cross-sectional view taken along the line A-A in FIG. 2, FIG. 5 is a perspective view illustrating an optical path using a pair of stereo cameras among the components illustrated in FIG. 2, and FIG. 6 is a plan schematic view illustrating the position design of a single polarizer filter among the components illustrated in FIG. 2.

As illustrated in FIGS. 1 to 4, the 3D intraoral scanner according to an embodiment of the present disclosure includes a housing 10 configured to be inserted into and withdrawn from an oral cavity.

At least one camera 20 may be disposed inside the housing 10. That is, although not shown in the figures, the at least one camera 20 may be disposed inside the housing 10 as a single camera 20. In addition, as illustrated in FIG. 3, the at least one camera 20 may be disposed inside the housing 10 as a pair of stereo cameras 20.

Here, in a case in which the at least one camera 20 is disposed as the pair of stereo cameras 20, the stereo cameras 20 may be disposed to be spaced apart from each other in the lateral direction of the housing 10 in order to allow light incident from one end of the housing 10 to pass therethrough along different paths. Hereinafter, for the convenience of explanation, it will be described on the assumption that the at least one camera 20 is disposed inside the housing 10. However, it should also be understood that the application of the single camera 20 is not completely excluded.

The term "light" used herein means light in the visible light range that may be recognized by the human eyes in a broad sense. However, light may also be a concept including either infrared (IR) radiation or ultraviolet (UV) radiation that may be observed using a specific optical device. In a narrow sense, light may mean the internal shape (hereinafter, briefly referred to as "image") of an oral cavity of a patient to be measured.

Thus, the housing 10 may have an open area 16 in one end thereof, the open area 16 allowing an image in the form of light to enter the housing 10 therethrough. The open area 16 may be an entrance through which light outside the housing 10 enters the housing 10. The light incoming through the open area 16 passes through each of the pair of stereo cameras 20 while forming different light paths. Imaging sensors 31b and 32b provided on imaging boards 31a and 32a capture an image from the light that has passed through the pair of stereo cameras 20.

Here, the image may be obtained as two pieces of image data at the same time. Thus, when the distance between the pair of stereo cameras 20 and the focal length of the target point captured by each of the corresponding stereo cameras 20 are known, 3D image data of the image may be obtained.

Although not specifically shown, the pair of stereo cameras 20 may include at least two transmission lenses, the focal lengths of which are adjustable with respect to the image within the oral cavity.

In this regard, a 3D intraoral scanner 1 according to an embodiment of the present disclosure may further include the imaging boards 31a and 32a including the imaging sensors 31b and 32b each of which image-processes the light that has passed through the pair of stereo cameras 20. In addition, the 3D intraoral scanner 1 according to an embodiment of the present disclosure may further include a camera control board on which electronic components for controlling the operation of the pair of stereo cameras 20 are mounted and a scanning control board on which electronic components for processing a scanned image are mounted.

As illustrated in FIGS. 2 to 4, the housing 10 serves to provide a predetermined space in which the pair of stereo cameras 20, the imaging boards 31a and 32a, the camera control board (not shown), and the scanning control board (not shown) are disposed.

More specifically, as illustrated in FIG. 3, the housing 10 includes a body housing 11 comprised of a lower housing 12 having defined therein a space in which the above-described components are disposed and an upper housing 13 provided above the lower housing 12 and detachably coupled to the lower housing 12 to cover the components.

In addition, the housing 10 may further include a tip housing 14 coupled to one end of the body housing 11, and having the above-described open area 16 and an incoming-exiting light path portion 17. The incoming-exiting light path portion 17 guides light entering the body housing 11 through the open area 16 and light exiting the body housing 11 through the open area 16.

The inside of the tip housing 14 is provided as a dark room 85 which light neither enters nor exits, as will be described below. The dark room 85 may be configured to have different lengths depending on the age group and the characteristics of the oral cavity of the patient to be measured.

For example, when the patient to be measured is a child, it is desirable that the entire length of the tip housing 14 is relatively short, and the dark room 85 in this case may also be fabricated such that the length thereof is relatively short.

In addition, when the patient to be measured is an adult, it is desirable that the entire length of tip housing 14 is relatively long, and the dark room 85 in this case may also be fabricated such that the length thereof is relatively long.

That is, the tip housing 14 coupled to one end of the body housing 11 may be fabricated in a variety of specifications so as to be provided with the dark room having different lengths depending on the length measured from one end to the other end, such that the tip housing 14 may be easily separated and replaced depending on the patient to be measured. Thus, the tip housing 14 may be detachably coupled to one end of the body housing 11.

Here, a single polarizer filter 80 described below is disposed in the dark room 85. The dark room 85 may be fabricated in a variety of lengths as long as a set distance d by which the position of the single polarizer filter 80 described below is set is met. Here, the single polarizer filter 80 may be previously fixed in different positions in which the set distance d is met, thereby allowing tip housings 14 having a variety of specifications to be used in a replaceable manner.

Here, light entering the body housing 11 through the open area 16 (hereinafter, referred to as "incoming light") means the image, i.e., the internal shape of the oral cavity of the patient, whereas light exiting the body housing 11 through the open area 16 (hereinafter, referred to as "exiting light") means irradiation light emitted by a light projector 70 described below.

A light guide structure may be provided inside the tip housing 14, which allows the incoming light and the exiting light to be easily emitted into and from the housing 10. In addition, the open area 16 may be configured to be opened in one direction perpendicular to the longitudinal direction of the tip housing 14, and a reflecting member 60 described below may be disposed in the open area 16.

The front ends of the pair of stereo cameras 20 may be disposed to converge to each other on the tip housing 14 side, as described above, so as to overlap with each other by a predetermined length toward the tip housing 14. In addition, the rear ends of the pair of stereo cameras 20 may be provided to be connected to a camera mount 50 fixed within the body housing 11.

In addition, as illustrated in FIGS. 3 and 4, the 3D intraoral scanner 1 according to an embodiment of the present disclosure may further include a light projector 70 disposed inside the housing 10 to emit exiting light through between the pair of stereo cameras 20. The light projector 70 emits the exiting light through the open area 16 provided in the front end of the tip housing 14 of the housing 10.

Furthermore, as illustrated in FIGS. 3 to 5, the 3D intraoral scanner 1 according to an embodiment of the present disclosure may further include a single polarizer filter 80 located between the pair of stereo cameras 20 and the open area 16, in a position spaced apart the set distance d from the front end of the pair of stereo cameras 20.

In the 3D intraoral scanner 1 according to an embodiment of the present disclosure, proposed is an optimum arrangement structure allowing the above-described components to be disposed inside the housing 10, proposing the body housing 11 to be fabricated in a slim profile such that a user may easily hold and use the 3D intraoral scanner 1 according to the present disclosure, and enabling the tip housing 14 to be formed as long and slim as possible so as to be easily inserted into and withdrawn from the oral cavity of the dental patient.

Here, the slim design of the body housing 11 relates to the arrangement design of the imaging sensors 31b and 32b respectively provided for incoming light entering through each of the pair of stereo cameras 20 as will be described below, whereas the slim design of the tip housing 14 relates to the arrangement design of the single polarizer filter 80 as will be described below.

Hereinafter, a scheme for the slim design of the body housing 11 will be described in more detail.

As illustrated in FIG. 3, the camera mount 50 may be disposed inside the housing 10 such that one end of each of the pair of stereo cameras 20 protrudes toward the tip housing 14 and the other ends of the pair of stereo cameras 20 are fitted into the camera mount 50. The camera mount 50 forms an optical waveguide serving as a path for incoming light that has passed through the pair of stereo cameras 20 or exiting light emitted by the light projector 70.

The optical waveguide formed in the camera mount 50 may be provided as a dark room such that incoming light entering through the open area 16 and exiting light emitted by the light projector 70 are isolated from each other so as not to interfere with each other.

That is, the optical waveguide may include an exiting light path portion 53 providing a light path reaching the tip housing 14 side for exiting light emitted by the light projector, one incoming light path portion 51 on one side providing a light path for incoming light entering through one camera of the pair of stereo cameras 20, and the other incoming light path portion 52 on the other side providing a light path for incoming light entering through the other camera of the pair of stereo cameras 20.

Here, the exiting light path portion 53, one incoming light path portion 51 on one side, and the other incoming light path portion 52 on the other side may be isolated from each other such that light in one light path is not influenced at all by light in other light paths.

Furthermore, the light projector is located on the central portion of the other ends of the pair of stereo cameras 20 disposed to be spaced apart a predetermined distance from each other in the lateral direction of the housing 10. The exiting light path portion 53 may be formed between one incoming light path portion 51 and the other incoming light path portion 52.

One incoming light path portion 51 and the other incoming light path portion 52 are formed in the longitudinal directions of the corresponding stereo cameras, respectively, such that incoming light entering from the pair of stereo cameras 20 may pass therethrough. Each of one incoming light path portion 51 and the other incoming light path portion 52 may be opened through one side surface and the other side surface of the camera mount 50.

Here, the imaging boards 31a and 32a on which imaging sensors 31b and 32b are integrated may be disposed vertically in the top-bottom direction so as to be in close contact with one side wall and the other side wall of the housing 10 in the lateral direction. More specifically, one of the imaging boards 31a and 32a may be disposed to be in close contact with one side surface of the camera mount 50, between one side wall of the housing 10 in the lateral direction and one side surface of the camera mount 50. In addition, the other of the imaging boards 31a and 32a may be disposed to be in close contact with the other side surface of the camera mount 50, between the other side wall of the housing 10 in the lateral direction and the other side surface of the camera mount 50. Here, one of the imaging boards 31a and 32a may be provided such that one of the imaging sensors 31b and 32b integrated thereon is exposed to one incoming light path portion 51, whereas the other of the imaging boards 31a and 32a may be provided such that the other of the imaging sensors 31b and 32b integrated thereon is exposed to the other incoming light path portion 52.

In addition, the 3D intraoral scanner 1 according to an embodiment of the present disclosure may further include a pair of light path changing mirrors 41 and 42 disposed to change the paths of incoming light that has passed through the pair of stereo cameras 20 toward the imaging sensors 31b and 32b integrated on the imaging boards 31a and 32a, respectively.

In the pair of light path changing mirrors 41 and 42, one light path changing mirror 41 on one side may be configured to change the path of incoming light that has passed through one incoming light path portion 51 to be emitted to one of the imaging sensors 31b and 32b integrated on one of the imaging boards 31a and 32a, whereas the other light path changing mirror 42 on the other side may be configured to change the path of incoming light that has passed through the other incoming light path portion 52 to be emitted to the other of the imaging sensors 31b and 32b integrated on the other of the imaging boards 31a and 32a.

Here, each of the pair of light path changing mirrors 41 and 42 may include a total reflection mirror (or a front surface mirror) able to totally reflect light. However, each of the pair of light path changing mirrors 41 and 42 is not necessarily limited to the total reflection mirror but may include any optical element able to totally reflect light.

The major technical feature of the 3D intraoral scanner 1 according to an embodiment of the present disclosure is to obtain 3D image data of the internal shape (i.e., image) of the oral cavity of a patient using the pair of stereo cameras 20.

However, as described above, one ends of the pair of stereo cameras 20 (referring to a direction in which the tip housing 14 is provided in the drawings) must be disposed to have angles converging to each other so as to be directed toward the reflecting member 60 provided in the single open area 16, whereas the other ends of the pair of stereo cameras 20 (referring to a direction in which the light projector 70 is provided in the drawings) must have a structure allowing incoming light to pass therethrough in linear directions.

Thus, the pair of imaging boards 31a and 32a must be disposed to be spaced apart from each other in the lateral direction of the housing 10 so as to be perpendicular to linear directions of the other ends of the pair of stereo cameras 20. However, in this case, the lateral thickness of the body housing 11 may be increased by the lengths of the pair of imaging boards 31a and 32a.

In the 3D intraoral scanner 1 according to an embodiment of the present disclosure, as described above, the incoming light path portions 51 and 52 are formed to be opened toward one side surface and the other side surface of the camera mount 50, respectively. The imaging boards 31a and 32a are vertically disposed in positions between one side surface and the other side surface of the camera mount 50 and one side wall and the other side wall of the housing 10. The pair of light path changing mirrors 41 and 42 changing the light paths of incoming light that has passed through the pair of stereo cameras 20 are provided. Thus, the body housing 11 may be formed slim such that an examiner may easily hold the body housing 11 with a thumb, an index finger, and a middle finger to use the 3D intraoral scanner 1.

The pair of light path changing mirrors 41 and 42 may be disposed to have reflector surfaces having angles at which incoming light that has passed through the pair of stereo cameras 20 is perpendicularly incident on one surface of each of the imaging sensors 31b and 32b provided on the pair of imaging boards 31a and 32a.

In this regard, the pair of light path changing mirrors 41 and 42 may be disposed such that the reflector surfaces are inclined with respect to the longitudinal direction of the housing 10. That is, one light path changing mirror 41 may be provided such that incoming light that has passed through one stereo camera 21 provided on one side enters through one incoming light path portion 51 and then is refracted from the reflector surface of one light path changing mirror 41 so as to be emitted to the imaging sensors 31b and 32b of one imaging board 31a. In the same manner, the other light path changing mirror 42 may be provided such that incoming light that has passed through the other stereo camera 22 provided on the other side enters through the other incoming light path portion 52 and then is refracted from the reflector surface of the other light path changing mirror 42 so as to be emitted to the imaging sensors 31b and 32b of the other imaging board 31b.

Next, a scheme for the slim design of the tip housing 14 will be described in more detail.

Figure 7:
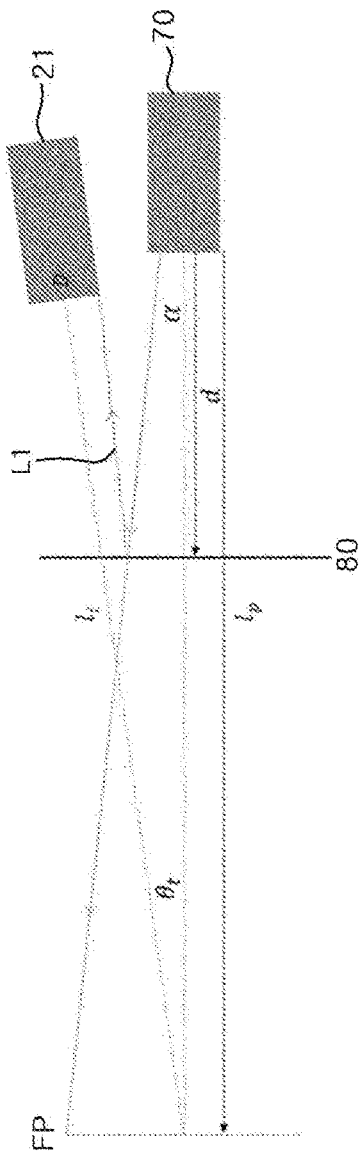
FIG. 7 is a schematic plan view illustrating the image angles of view, the projection angle of view, and the triangulation angle illustrated in FIG. 6.

FIG. 6 is a plan schematic view illustrating the position design of a single polarizer filter among the components illustrated in FIG. 2, and FIG. 7 is a schematic plan view illustrating image angles of view 92a and 92b, a projection angle of view 91, and triangulation angles illustrated in FIG. 6.

In the 3D intraoral scanner according to an embodiment of the present disclosure, as illustrated in FIGS. 3 to 5, the pair of stereo cameras 20 may be provided on the front end side of the body housing 11 to overlap a predetermined length with a portion on which the tip housing 14 is provided, and the light projector 70 may be disposed such that light is emitted through between the pair of stereo cameras 20.

Here, the 3D intraoral scanner according to an embodiment of the present disclosure may be provided with the single polarizer filter 80 configured to remove reflection light of a measurement object 100, such as a tooth, made of an internal reflection material and allow only surface reflection light to pass therethrough by filtering.

The single polarizer filter 80 may be disposed to be located on the tip housing 14 of the housing 10. More specifically, as illustrated in FIG. 4, a top fitting rib (not shown) and a bottom fitting rib 81 may be integrally formed inside the tip housing 14. That is, the single polarizer filter 80 may be disposed such that the top end and the bottom end thereof are fitted to the top fitting rib and the bottom fitting rib 81 integrally formed inside the tip housing 14.

The single polarizer filter 80 may be located inside the tip housing 14, between the pair of stereo cameras 20 and the open area 16, in a position spaced apart the set distance d from the front ends of the pair of stereo cameras 20.

More specifically, as illustrated in FIG. 6, the set distance d of the single polarizer filter 80 may be set to a distance in which the projection angle of view 91, at which light emitted by the light projector 70 is projected, and the image angles of view 92a and 92b in two locations, at which light reflected from the measurement object 100 enters the pair of stereo cameras 20, do not overlap with each other.

That is, as illustrated in FIG. 6, light exiting the light projector 70 passes through the single polarizer filter 80 and then is projected into the oral cavity of the patient, in which the measurement object 100 is located, through the open area 16. Here, a maximum area of the single polarizer filter 80 through which the light exiting the light projector 70 has passed may be defined as the projection angle of view 91 as described above.

In addition, the light projected into the oral cavity of the patient after exiting the light projector 70 is introduced back into the tip housing 14 through the open area 16 as reflection light reflected from the measurement object 100. Then, the light enters each of the pair of stereo cameras 20 spaced apart from each other in the lateral direction of the body housing 11. Here, maximum areas of the single polarizer filter 80 through which the light passes to enter each of the pair of stereo cameras 20 may be defined as the image angles of view 92a and 92b as described above.

Here, when the position in which the single polarizer filter 80 is disposed is set to be a position in which the projection angle of view 91 and the image angles of view 92a and 92b overlap with each other, the light projected by the light projector 70 may be reflected from a transmission surface of the single polarizer filter 80 to enter the pair of stereo cameras 20. In this case, an image obtained through the imaging sensors 31b and 32b may be a ghost image or noise having an image point brighter than surrounding images.

Thus, the 3D intraoral scanner 1 according to an embodiment of the present disclosure may be designed such that the set distance d is set to a position in which the projection angle of view 91 and the image angles of view 92a and 92b, formed by passage of light through the single polarizer filter 80, do not overlap each other in order to prevent the ghost image or noise from occurring.

That is, the set distance d defining the position of the single polarizer filter 80 may be set such that light projected into the oral cavity by the light projector 70 does not enter each of the pair of stereo cameras as reflection light reflected by the single polarizer filter 80.

Theoretically, the set distance d is only required to be set such that the single polarizer filter 80 is located in the range in which the projection angle of view 91 and the image angles of view 92a and 92b do not overlap with each other. Thus, the single polarizer filter 80 may be located as close as possible to the front ends of the pair of stereo cameras 20. However, in this case, the original purpose for fabricating the tip housing 14 in a slim profile is not obtained, which is problematic.

That is, in an embodiment of the present disclosure, when a single camera is applied, at least the size of the single polarizer filter 80 is required to be physically greater than the size of either the projection angle of view 91 or the image angle of view (refer to one of reference numerals 92a and 92b in FIG. 6) described above. In a case in which the single polarizer filter 80 is designed to be located as close as possible to the front ends of a single camera, an unavoidable increase in the lateral direction is expected.

In addition, in an embodiment of the present disclosure, when the pair of stereo cameras 20 are applied in order to overcome the drawbacks occurring during the use of the single camera as described above, the pair of stereo cameras 20 are disposed in the lateral direction of the body housing 11 such that the front ends of the pair of stereo cameras 20 overlap with the tip housing 14. Here, the single polarizer filter 80 must be fabricated in a size that may be realized by at least the image angles of view 92a and 92b. When the single polarizer filter 80 is designed to be as close as possible to the pair of stereo cameras 20 as described above, the lateral size thereof must be unavoidably increased, thereby causing a problem in that the slim design of the tip housing 14 is inhibited.

In the 3D intraoral scanner 1 according to an embodiment of the present disclosure, in order to solve the above-described problem, the set distance d of the single polarizer filter 80 may be set to a position in which the entire size of the single polarizer filter 80 is smallest on the premise that the vertical width and the lateral width (hereinafter, briefly referred to as the "entire size") of the single polarizer filter 80 increase as the single polarizer filter 80 is closer to the pair of stereo cameras 20.

In addition, in the 3D intraoral scanner 1 according to an embodiment of the present disclosure, even if the single polarizer filter 80 is moved closer to the pair of stereo cameras 20 to have the minimum distance, a position in which the single polarizer filter 80 does not have mechanical or structural interference with the surrounding components must be set.

In this regard, as illustrated in FIG. 7, the optimum set distance d of the single polarizer filter 80 may be set to meet the following Formula:

$$d < \frac{\left(l_i Q_t - \frac{D}{2}\right)}{2\tan\alpha} + \frac{(l_p - l_i)}{2} \quad \text{[Formula 1]}$$

Here, d is a set distance, $l_p$ is a distance from the light projector to the image, $l_i$ is a distance from the lens of one camera to the image, $Q_t$ is a triangulation angle, D is the diameter of the lens of one camera, and $\alpha$ is a projection angle of view.

According to Formula 1 above, it is more desirable that the set distance d is smaller. Thus, the single polarizer filter 80 may be located as close as possible to the pair of stereo cameras 20 at the minimum distance in which the single polarizer filter 80 does not mechanically interfere with the pair of stereo cameras 20.

However, as described above, when the single polarizer filter 80 is close to the pair of stereo cameras 20, the problem of the increased entire size may occur. Thus, also in this case, the design must be accomplished in consideration of the slim profile fabrication according to the purpose of the embodiment of the present disclosure.

Here, referring to FIG. 7, D is the diameter of the lens of one camera 21. An increase in D means that the set distance d must be designed to be smaller and is an impediment to the slim design. Thus, it is desirable that D is designed to be as small as possible, and for each of the light projector 70 and the pair of stereo cameras 21 and 22, an optimum mechanical design preventing the mechanical interference must be prioritized.

Furthermore, as illustrated in FIG. 7, the 3D intraoral scanner according to an embodiment of the present disclosure must meet a condition in which reflection light L1 should not be directly incident on the camera 21 through the single polarizer filter 80 defining the projection angle of view 91. Here, an increase in the diameter D of the lens of one camera 21 causes an increase in the image angle of view 92b. In this case, the projection angle of view 91 and the image angle of view 92b may overlap with each other. Thus, the set distance d must be designed to be smaller.

Formula 1 above proposes a theoretical background by which the optimum set distance d of the single polarizer filter 80 able to realize all of these purposes is obtained.

In addition, as described above, the reflecting member 60 may be provided in the open area 16 of the tip housing 14. The reflecting member 60 serves to reflect incoming light entering the body housing 11 and exiting light emitted from inside the body housing 11 along predetermined paths. This reflecting member 60 may be provided in the shape of a mirror or a prism.

In particular, the reflecting member 60 allows the pair of stereo cameras 20 to easily capture images through the open area 16 opened in one direction perpendicular to the longitudinal direction of the housing 10.

Here, the single polarizer filter 80 is located between the pair of stereo cameras 20 and the reflecting member 60 to be parallel to the light projector 70. The single polarizer filter 80 being disposed parallel to the light projector 70 means that, when polarizer filters are provided on a light path for light exiting from the light projector 70 and light paths for light incident on the camera lenses, respectively, a complicated conventional process of designing the positions of the polarizer filters to cope with reduced polarization efficiency in a very sophisticated manner may be advantageously omitted.

The operation of the 3D intraoral scanner 1 having the above-described configuration according to the present disclosure will be described in more detail with reference to the accompanying drawings (in particular, FIGS. 3 to 6). The examiner presses an operation button 15 provided on the top portion of the housing 10 in order to measure the inside of the oral cavity of a patient using the 3D intraoral scanner 1 according to an embodiment of the present disclosure.

Then, as illustrated in FIGS. 5 and 7, exiting light is emitted by the light projector 70. The exiting light emitted by the light projector 70 is emitted toward the open area 16 sequentially through the exiting light path portion 53 of the optical waveguide provided in the camera mount 50 and the incoming-exiting light path portion 17 provided in the tip housing 14 and then is emitted into the oral cavity of the patient through the open area 16 by the reflecting member 60.

At the same time, as illustrated in FIGS. 5 and 6, the pair of stereo cameras 20 may be operated by the examiner operation of pressing the operation button 15, thereby obtaining two pieces of image data having a single point on the image as a common focus.

At this time, the image of the oral cavity of the patient is present in the form of light due to the exiting light. Contrast to the exiting light, the light enters the tip housing 14 through the open area 16, the path of the light is changed by the reflecting member 60, and then, the light enters each of the lenses of the pair of cameras substantially capturing images from the reflecting surfaces of the reflecting member 60 through the incoming-exiting light path portion 17, the corresponding stereo cameras, and the corresponding incoming light path portions 51 and 52 of the optical waveguide as described above. In addition, the light is emitted to the imaging sensors 31b and 32b of the corresponding imaging boards 31a and 32a by the light path changing mirrors 41 and 42, and thus, two pieces of image data may be obtained simultaneously. On the basis of the two pieces of image data obtained in this manner, 3D data of the image of the oral cavity of the patient may be easily obtained.

Figure 8:
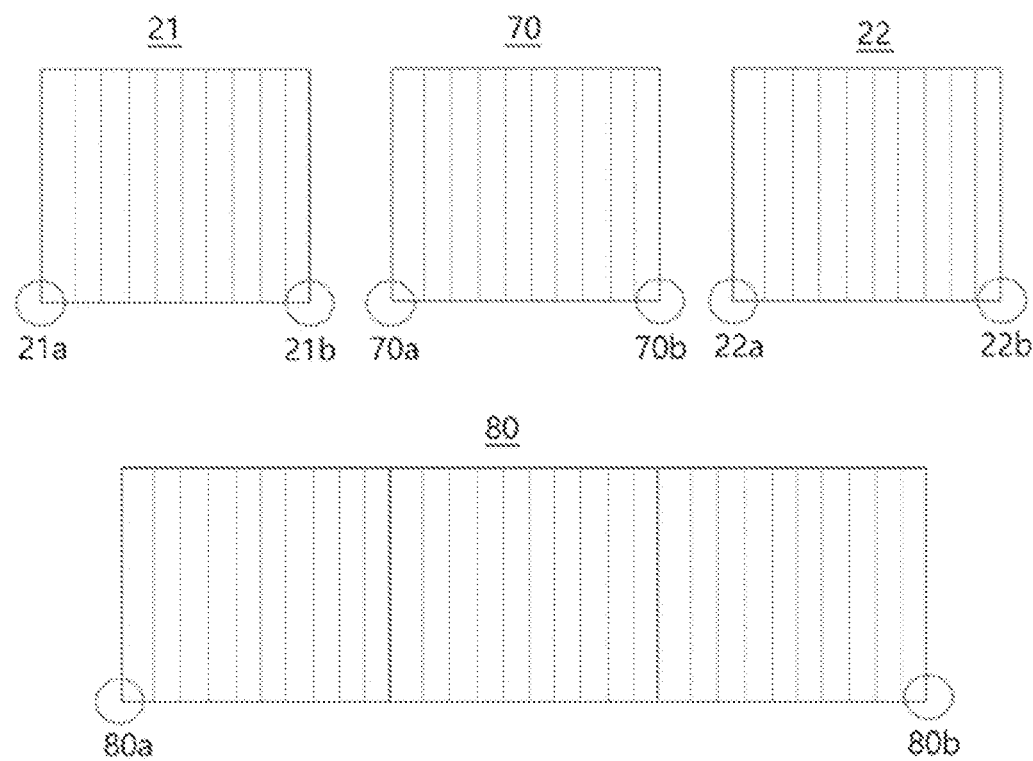
FIG. 8 is a schematic view illustrating fixing portions of at least one camera and a light projector and fixing portions of a single polarizer filter among the components of the 3D intraoral scanner according to an embodiment of the present disclosure.
Figure 9:
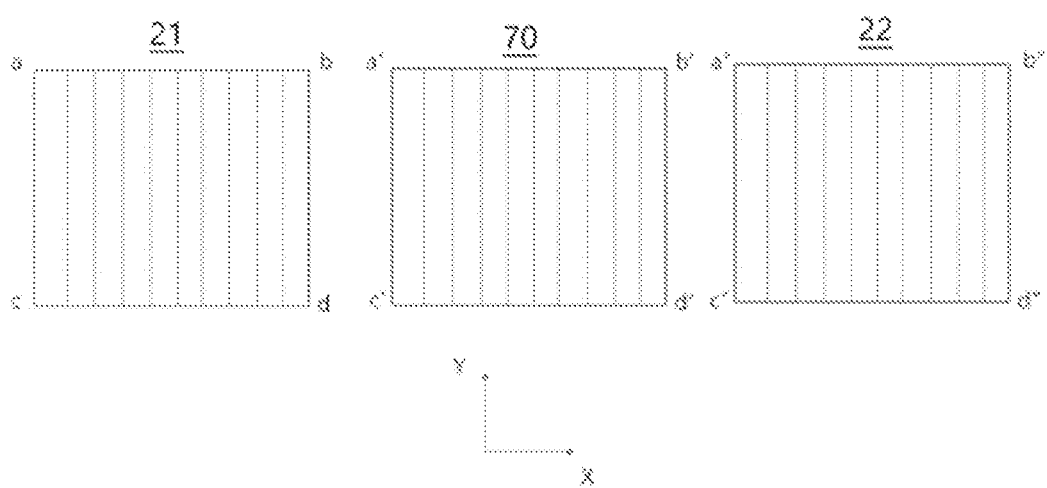
FIG. 9 is a schematic view illustrating an ideal installation model of the at least one camera and the light projector among the components illustrated in FIG. 8.
Figure 10:
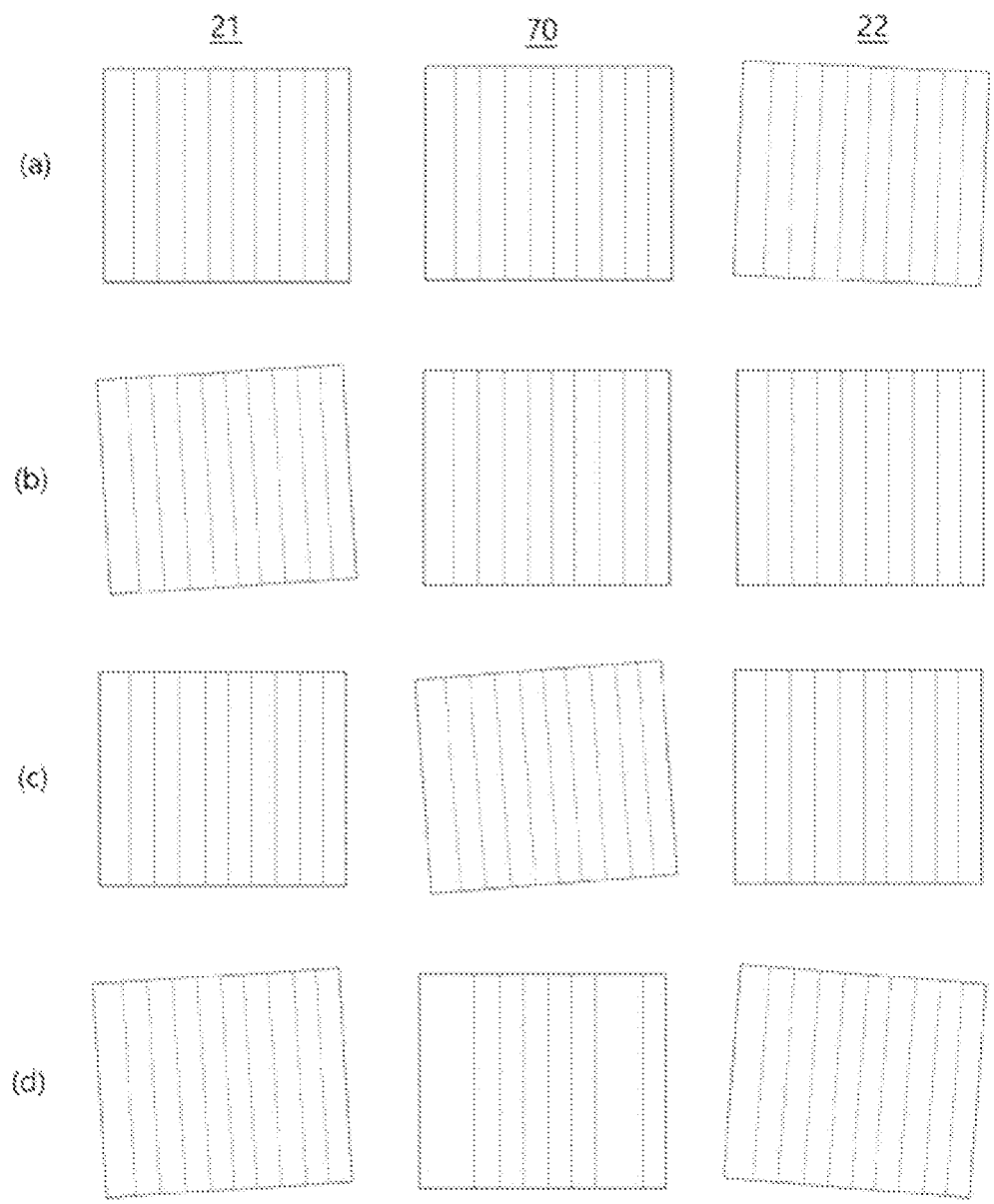
FIG. 10 is a variety of schematic views illustrating the occurrence of tolerances when the at least one camera and the light projector among the components illustrated in FIG. 8 are disposed.
Figure 11:
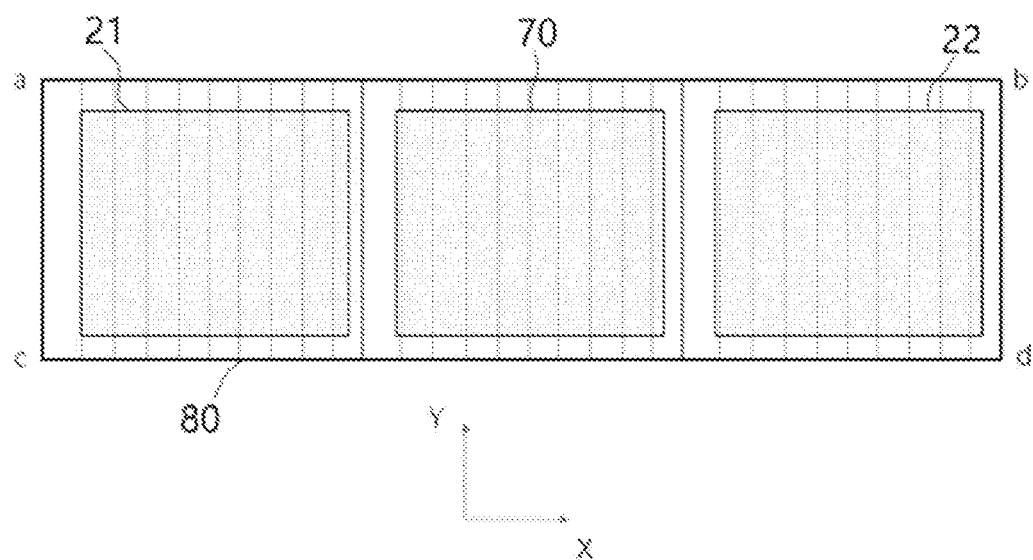
FIG. 11 is a schematic view illustrating an effect obtained using the single polarizer filter.
Figure 12:
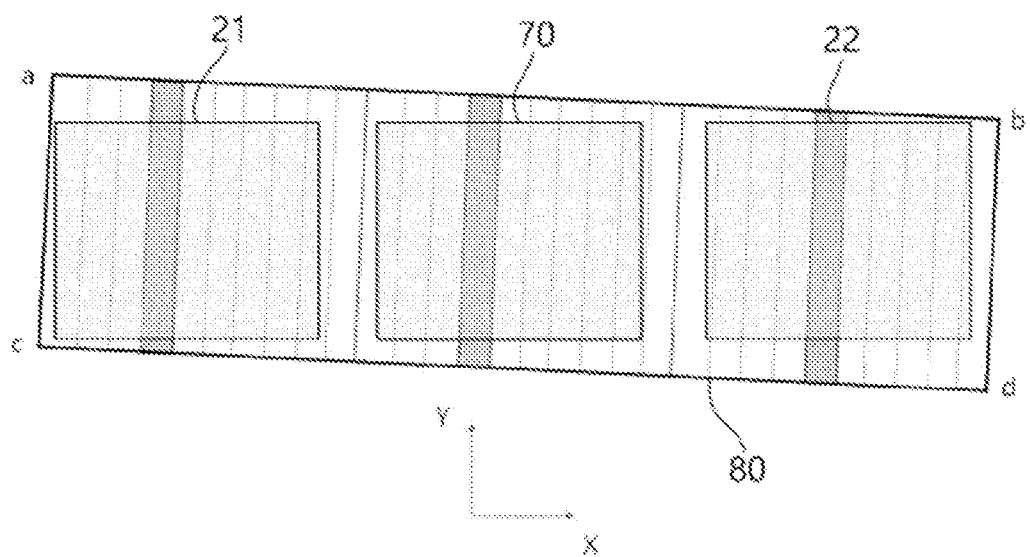
FIG. 12 is a schematic view illustrating another effect obtained using the single polarizer filter.

FIG. 8 is a schematic view illustrating fixing portions of at least one camera and a light projector and fixing portions of a single polarizer filter among the components of the 3D intraoral scanner according to an embodiment of the present disclosure, FIG. 9 is a schematic view illustrating an ideal installation model of the at least one camera and the light projector among the components illustrated in FIG. 8, FIG. 10 is a variety of schematic views illustrating the occurrence of tolerances when the at least one camera and the light projector among the components illustrated in FIG. 8 are disposed, FIG. 11 is a schematic view illustrating an effect obtained using the single polarizer filter, and FIG. 12 is a schematic view illustrating another effect obtained using the single polarizer filter.

FIGS. 8 to 12 are schematic views illustrating effective aspects of the 3D intraoral scanner according to an embodiment of the present disclosure. As illustrated in FIG. 8, it is most desirable that bottom ends of one stereo camera 21, the other stereo camera 22, the light projector 70 between the stereo cameras 21 and 22, and the single polarizer filter 80 provided inside the body housing 14 may be disposed in predetermined fixing positions (see reference numerals 21a, 21b, 22a, 22b, 70a, 70b, 80a, and 80b in FIG. 8) without allowance.

However, as illustrated in FIG. 9, the installation of the configuration of the single polarizer filter 80 may not be premised. In this case, the projection angle of view 91, at which light emitted by the light projector 70 is projected, and the image angles of view 92a and 92b in two locations, at which light reflected from the measurement object 100 enters one stereo camera 21 and the other stereo camera 22, are required to not overlap with each other. For this, from the installation step, polarizer filters (not shown) corresponding to the light projector 70 and the stereo cameras 21 and 22, respectively, must be provided parallel to the XY axes. Here, the polarizer filters are fixed to at least meet a=a'=a", b=b'=b", c=c'=c", and d=d'=d". Furthermore, even if the polarizer filters are not installed with ideal values as described above, the polarizer filter must at least meet lines ac=a'c'=a"c".

However, when the one stereo camera 21, the other stereo camera 22, and the light projector 70 illustrated in FIG. 9 are actually installed, various types of allowances, such as an assembly allowance, may occur.

That is, among three components, the other stereo camera 22 may have an assembly allowance as illustrated in FIG. 10 (a), one stereo camera 21 may have an assembly allowance as illustrated in FIG. 10 (b), only the light projector 70 may have an assembly allowance as illustrated in FIG. 10 (c), or one stereo camera 21 and the other stereo camera 22 may have an assembly allowance as illustrated in FIG. 10 (d).

As described above, when the single polarizer filter 80 according to an embodiment of the present disclosure is not applied and the respective polarizer filters are applied, there is a problem in that the accuracies of measured values may be lowered due to the assembly allowances or the like of these three components.

For example, assuming that projection light polarized through the light projector 70 is 100%, reflection light reflected from a measurement object must be (100-@)%, due to mechanical allowances on both sides, i.e., mechanical allowances between one stereo camera 21 and the corresponding polarizer filter and between the other stereo camera 22 and the corresponding polarizer filter.

However, when the single polarizer filter 80 provided in a position meeting the set distance d as in an embodiment of the present disclosure is applied, it is only required that x values, i.e., a=c and b=d components, are the same and y values, i.e., a=b and c=d components, are the same as illustrated in FIG. 11. Compared to the case in which the respective polarizer filters are applied, there is an advantage in that the design of a mechanism for the same position adjustment may be very easily calculated.

Furthermore, as illustrated in FIG. 12, even in the case that the single polarizer filter 80 has an installation allowance, a portion of the light projector 70 corresponding to the projection angle of view and portions corresponding to the image angles of view have the same angle, like shades marked on portions corresponding to the image angles of view and the projection angle of view. Accordingly, it may be understood that the efficiency of the projection light is the same as that of the reflection light.

Here, the size of the projection angle of view of the light projector 70 and the sizes of the image angles of view of one stereo camera 21 and the other stereo camera 22 are adjusted according to the foregoing Formula and thus do not exceed the area of the single polarizer filter 80. Accordingly, there is an advantage in that reliability is significantly improved.

As set forth above, the 3D intraoral scanner according to an embodiment of the present disclosure has been described in detail with reference to the accompanying drawings. However, embodiments of the present disclosure are not limited to the foregoing embodiment and those skilled in the technical field, to which the present disclosure pertains, will make various modifications and equivalents without departing from the scope of the present disclosure. The true scope of right of the present disclosure shall be defined by the appended Claims.

INDUSTRIAL APPLICABILITY

The present disclosure provides a 3D intraoral scanner configured to obtain 3D image data of a measurement object simultaneously with measuring the measurement object, wherein a body housing can be fabricated to be slim so that a user can easily hold the body housing.

The invention claimed is:

1. A three-dimensional intraoral scanner comprising:
a housing configured to be inserted into and withdrawn from an oral cavity, and comprising an open area in one end thereof, the open area allowing an internal shape (hereinafter, referred to as an image) of the oral cavity to enter the housing as light;
at least one camera disposed inside the housing, and configured to allow light entering through the open area of the housing to pass therethrough;
a light projector disposed on one side of the at least one camera to emit light into the oral cavity through the open area; and
a single polarizer filter located between the at least one camera and the open area and disposed parallel to the light projector, wherein the single polarizer filter is located in a position spaced apart a set distance (d) from a front end of the at least one camera.

2. The three-dimensional intraoral scanner of claim 1, wherein the set distance (d) is set to a distance in which a projection angle of view, at which light is projected into the oral cavity by the light projector, and an image angle of view, at which light reflected from inside the oral cavity enters the at least one camera, do not overlap with each other.

3. The three-dimensional intraoral scanner of claim 1, wherein the set distance (d) is set such that light projected into the oral cavity by the light projector does not enter the at least one camera as reflection light reflected by the single polarizer filter.

4. The three-dimensional intraoral scanner of claim 1, wherein the set distance (d) is set to a position in which the entire size of the single polarizer filter is smallest on the premise that the vertical width and the lateral width (hereinafter, briefly referred to as the "entire size") of the single polarizer filter increase as the single polarizer filter is closer to the at least one camera.

5. The three-dimensional intraoral scanner of claim 1, wherein the set distance (d) meet the following formula:

$$d < \frac{\left(l_i Q_t - \frac{D}{2}\right)}{2\tan\alpha} + \frac{(l_p - l_i)}{2},$$

where d is the set distance, $I_p$ is a distance from the light projector to the image, $I_i$ is a distance from the lens of the camera on one side to the image, $Q_t$ is a triangulation angle, D is the diameter of the lens of the camera on one side, and $\alpha$ is a projection angle of view.

6. The three-dimensional intraoral scanner of claim 1, wherein the housing comprises:
a body housing in which the at least one camera and a variety of electronic components for driving the at least one camera are disposed; and
a tip housing coupled to one end of the body housing, the open area being provided in the tip housing,
wherein the single polarizer filter is disposed such that the set distance (d) is positioned in the tip housing.

7. The three-dimensional intraoral scanner of claim 6, wherein a top fitting rib and a bottom fitting rib are integrally provided inside the tip housing, top and bottom ends of the single polarizer filter being fitted to the top fitting rib and the bottom fitting rib.

8. The three-dimensional intraoral scanner of claim 6, wherein the tip housing in which the set distance (d) is positioned is fabricated in a variety of specifications to be provided with a dark room having different lengths depending on a length measured from one end to the other end; and the tip housing is detachably coupled to one end of the body housing so as to facilitate detachment from and replacement to one end of the body housing.

9. The three-dimensional intraoral scanner of claim 8, wherein the tip housing is configured such that the single polarizer filter is previously fixed in different positions meeting the set distance (d) depending on the length of the dark room.

10. A three-dimensional intraoral scanner comprising:
a housing configured to be inserted into and withdrawn from an oral cavity, and comprising an open area in one end thereof, the open area allowing an internal shape (hereinafter, referred to as an image) of the oral cavity to enter the housing as light;
at least one camera disposed inside the housing, and configured to allow light entering through the open area of the housing to pass therethrough;
a light projector disposed on one side of the at least one camera to emit light into the oral cavity through the open area; and
a single polarizer filter located between the at least one camera and the open area and disposed parallel to the light projector, wherein the single polarizer filter is horizontally disposed such that a projection angle of view projected into the oral cavity by the light projector and an image angle of view reflected from inside the oral cavity and entering the at least one camera do not overlap with each other.

11. A three-dimensional intraoral scanner comprising:
a housing configured to be inserted into and withdrawn from an oral cavity, and comprising a reflecting member reflecting incoming light entering the body housing and exiting light emitted from inside the body housing;
a pair of stereo cameras disposed inside the housing, and configured to allow the incoming light entering through the reflecting member of the housing to pass therethrough along different paths;
a light projector disposed between the pair of stereo cameras, and configured to emit the exiting light into the oral cavity through the reflecting member; and
a single polarizer filter located between the pair of stereo cameras and the reflecting member, and disposed parallel to the light projector.

* * * * *